United States Patent [19]

McCarty

[11] 4,069,346

[45] Jan. 17, 1978

[54] COMPOSITIONS AND METHODS FOR ANESTHETIZING AN ANIMAL USING DEUTERATED ANALOGUES OF HALOTHANE AND CHLOROFORM

[75] Inventor: Leslie P. McCarty, Midland, Mich.

[73] Assignee: The Dow Chemical Company, Midland, Mich.

[21] Appl. No.: 768,307

[22] Filed: Feb. 14, 1977

[51] Int. Cl.$^2$ .............................................. A61K 31/02
[52] U.S. Cl. .................................................... 424/350
[58] Field of Search ........................................ 424/350

[56] References Cited

PUBLICATIONS

Hine et al., Jacs, vol. 83, No. 5, Mar. 5, 1961, pp. 1219–1222.

*Primary Examiner*—Jerome D. Goldberg
*Attorney, Agent, or Firm*—James W. Ambrosius

[57] ABSTRACT

Deuterated analogues of halothane and chloroform are used to anesthetize an animal.

6 Claims, No Drawings

COMPOSITIONS AND METHODS FOR ANESTHETIZING AN ANIMAL USING DEUTERATED ANALOGUES OF HALOTHANE AND CHLOROFORM

BACKGROUND OF THE INVENTION

Halothane (2-bromo-2-chloro-1,1,1-trifluorethane) and chloroform are two commonly used general inhalation anesthetics. A major disadvantage of these compounds is that in some instances they cause damage to the liver. This toxicity is believed to result from the presence of toxic metabolites in the liver. See Anesth. 45, 622 (1976) and 43, 392 (1975). The metabolism of halothane also results in the elevation of inorganic bromide in the blood. See *Anesthes.* 44, 194 (1976). The elevation of plasma bromide is responsible for post-anesthetic depression.

It is known that the replacement of hydrogen by deuterium in some antimicrobial compounds will result in a marked decrease in enzymatic difluorination. See 15th Interscience Conf. of Antimicrobials, Agents and Chemotherap., September 24–26, 1975, Abstract Nos. 100, 101, and 102. A method of making deutrated halothane is disclosed in JACS 83, 1223 (1961).

SUMMARY OF THE INVENTION

It has been discovered that the deuterated analogues of halothane and chloroform significantly reduce the metabolism of the compounds to inorganic halogens when the deuterated anlogue is inhaled by an animal, especially a mammal. As used herein, the term "animal" refers to an inhalation anesthetic susceptible animal.

In anesthetizing an animal using the method of the present invention, the deuterated analogues are usually administered by vaporization of the compound in the presence of an innocuous gas vaporization medium such as, for example, helium, nitrogen, oxygen or various mixtures thereof. The compounds may also be used in combination with other anesthetics such as, for example, nitrous oxide.

From the foregoing discussion, it is seen that the deuterated analogues of halothane and chloroform have substantially the same desirable anesthetic effects as halothane and chloroform, respectively, but are not as readily metabolized by an animal which has inhaled them. Accordingly, the possibility of hepatic toxicity and in the case of halothane plasma bromide induced anesthetic depression is significantly reduced by using the deuterated analogues as an anesthetic.

DETAILED DESCRIPTION OF THE INVENTION

The following examples will serve to further clarify the present invention but are not to be construed as a limitation thereon.

EXAMPLE 1

Preparation of 2-bromo-2-chloro-1,1,1-trifluoroethane-d

A 1 liter flask was fitted with a mechanical stirrer and a reflux condenser. The flask was charged with 250 ml (465 grams) of 2-bromo-2-chloro-1,1,1-trifluoroethane, 200 ml of heavy water ($D_2O$) and 4 grams of sodium hydroxide. The resulting mixture was stirred overnight. A sample from the organic layer confirmed by NMR that about 95% of the hydrogen had been replaced by deuterium.

The organic layer was washed with water and dried over calcium chloride. Analysis with a gas chromatograph confirmed a purity in excess of 99%.

EXAMPLE 2

Halothane and deuterated halothane were vaporized by metering the liquid compounds at a controlled rate into a temperature regulated vaporization flask held at 150° C. The vapor was swept into the air inlet of a 30 liter glass exposure chamber at a rate of 6 liters/minute. The concentration of the anesthetic in the exposure chamber was monitored by gas-liquid chromatography using direct gas sampling loops.

Three groups of 6 male Fischer 344 rats (6 months of age, 200–300 grams) were exposed to room air and 0.75 volume/$_{volume}$ halothane or the deuterated analogue for a period of 2 hours. Following exposure, all animals were maintained for 72 hours. At the end of this period, the animals were decapitated and the blood collected in plastic centrifuge tubes where it was allowed to clot. The serum inorganic bromide concentration was determined using a specific ion electrode (Orion). Inorganic serum bromide concentrations for each group of animals were compared with the other groups by analysis of variance.

The serum inorganic bromide of the control group (room air only) was 0.5 m Eq./1 ± 0.02; halothane was 1.9 m Eq./1 ± 0.1; and deuterated halothane was 1.6 m Eq./1 ± 0.1. The serum bromide levels of the rats treated with halothane were significantly higher than those treated with deuterated halothane, $p<0.01$.

No difference in anesthetic properties was noted between halothane and the deuterated analogue.

EXAMPLE 3

The relative hepatotoxicity of chloroform was demonstrated using the method described by Klassen and Plaa, *Toxicol. Appl. Pharmacol.*, 9, 139–151 (1966), which used the serum glutamic-pyruvic transaminase (SGPT) level as an indicator of liver damage.

Using the same equipment to expose the animals as that of Example 2, three groups of 10 male Fischer 344 rats were exposed to room air, 0.36 percent (v/v) chloroform and 0.36 percent (v/v) deuterated chloroform for two hours. The animals were maintained two to a cage for 24 hours following the exposure. At the end of this period, the animals were decapitated and blood was collected in plastic centrifuge tubes and allowed to clot. The SGPT levels were determined using a commercially available method. SGPT concentrations of each group of animals were compared with the other groups by nonparametric analysis of variance. The SGPT level of the control group was 24.8 m$\mu$/ml ± 2; chloroform was 56.3 m$\mu$/ml ± 24; and deuterated chloroform was 38.3 m$\mu$/ml ± 7. The difference between the chloroform treated group and the deuterated chloroform treated group was significant at $p<0.05$. In addition, no difference in the anesthetic properties of chloroform and deuterated chloroform was noted.

EXAMPLE 4

Using the same techniques as described in Example 3 above, Fischer 344 rats were anesthetized for two hours with halothane and deuterated halothane using an anesthetic concentration of 1 percent (v/v) in air. After 24 hours, the animals were sacrificed and the blood collected from each. SGPT was run on each blood sample as in indication of liver toxicity. The values were as follows:

| Treatment | SGPT mµ/ml |
|---|---|
| Control | 18.8 |
| Halothane | 24.0 |
| Deuterated Halothane | 19.6 |

It will be seen halothane produced a significant increase in SGPT levels, but the deuterated halothane was not significantly different from the control.

It is understood that various modifications may be made in the exact mode of carrying out the present invention without departing from the spirit and scope thereof. While the foregoing description has been directed to rats, it will be realized by one skilled in the art that the deuterated analogues of chloroform and halothane may be used with equal facility on other inhalation anesthetic susceptible animals.

I claim:

1. The process for anesthetizing an animal which comprises administering to said animal by inhalation an effective anesthetizing amount of the compound 2-bromo-2-chloro-1,1,1-trifluoroethane-d as a general inhalation anesthetic.

2. The process of claim 1 wherein the compound is administered to the animal by vaporization of the compound in the presence of an innocuous gas vaporization medium.

3. The process of claim 2 wherein the compound is administered in the presence of oxygen.

4. An inhalation anesthetic composition comprising the compound 2-bromo-2-chloro-1,1,1-trifluoroethane-d and an innocuous gas vaporization medium in suitable proportions for the production of anesthesia.

5. The anesthetic composition of claim 4 wherein the innocuous gas vaporization medium contains oxygen.

6. The anesthetic composition of claim 5 further including another anesthetic.

* * * * *